United States Patent
Hamilton et al.

(10) Patent No.: US 9,502,205 B2
(45) Date of Patent: Nov. 22, 2016

(54) X-RAY-GENERATING MEDICAL APPARATUS AND ACQUISITION WINDOW THEREFOR WITH A RELEASABLE ATTACHMENT TO THE MEDICAL APPARATUS

(71) Applicant: Siemens Aktiengesellschaft, Munich (DE)

(72) Inventors: Kathrin Friederike Hamilton, Forchheim (DE); Hans-Juergen Mueller, Pretzfeld (DE); Dominik Trautner, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 198 days.

(21) Appl. No.: 14/503,807

(22) Filed: Oct. 1, 2014

(65) Prior Publication Data
US 2015/0092909 A1    Apr. 2, 2015

(30) Foreign Application Priority Data
Oct. 1, 2013 (DE) .................. 10 2013 219 884

(51) Int. Cl.
*A61B 6/00* (2006.01)
*H01J 35/18* (2006.01)
*A61B 6/03* (2006.01)
*H05G 1/04* (2006.01)

(52) U.S. Cl.
CPC ............... *H01J 35/18* (2013.01); *A61B 6/035* (2013.01); *A61B 6/4435* (2013.01); *H05G 1/04* (2013.01); *H01J 2235/16* (2013.01)

(58) Field of Classification Search
CPC ..... A61B 6/035; A61B 6/4435; H01J 35/18; H01J 2235/16; H05G 1/04
USPC .............................................. 378/4–20, 140
See application file for complete search history.

(56) References Cited

U.S. PATENT DOCUMENTS 5,872,364 A    2/1999  Strommer
2010/0177867 A1*  7/2010  Kozelj ................... A61B 6/035
                                                               378/20

FOREIGN PATENT DOCUMENTS

JP        2005006806 A    1/2005
JP        2006071321 A    3/2006
WO     WO-2008/021662 A2  2/2008

* cited by examiner

*Primary Examiner* — Courtney Thomas
(74) *Attorney, Agent, or Firm* — Schiff Hardin LLP

(57) ABSTRACT

An acquisition window for a medical apparatus (in particular for a computer tomography apparatus) has an element made of a suitable material and at least one attachment element for attachment to the medical apparatus.

15 Claims, 3 Drawing Sheets

FIG 2
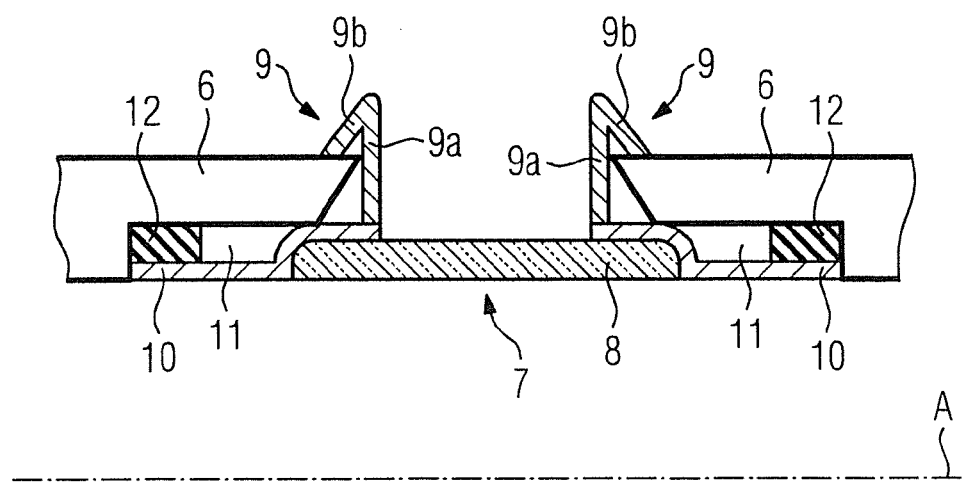
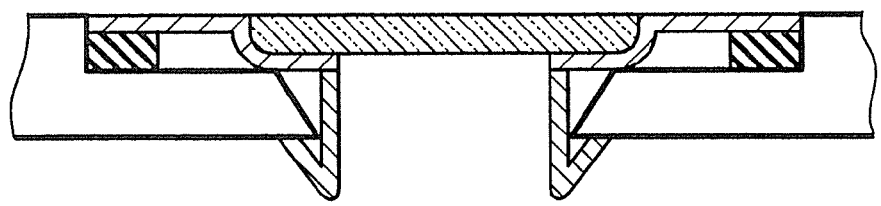

FIG 3
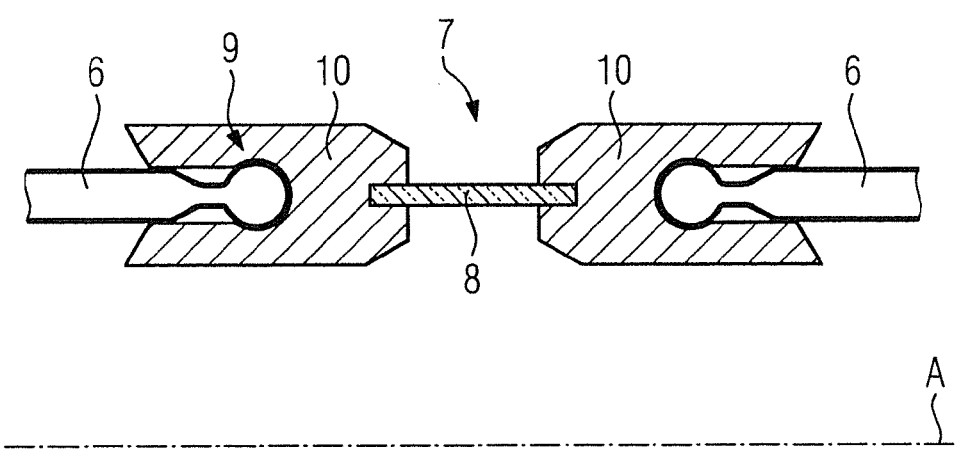
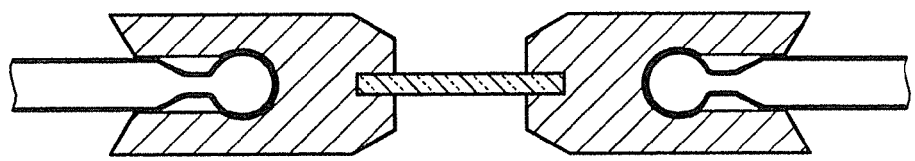

X-RAY-GENERATING MEDICAL APPARATUS AND ACQUISITION WINDOW THEREFOR WITH A RELEASABLE ATTACHMENT TO THE MEDICAL APPARATUS

BACKGROUND OF THE INVENTION

Field of the Invention

The present invention concerns an acquisition window for a medical apparatus, in particular for a computed tomography apparatus, of the type of an element made of a suitable material (in particular an x-ray-permeable material such as a ring or a strip of such material) and at least one attachment element to attach the element to a medical apparatus (in particular to a computed tomography apparatus). Furthermore, the invention concerns a medical apparatus (in particular a computed tomography apparatus) with such an acquisition window.

Description of the Prior Art

The present invention is explained in the context of the example of a computed tomography apparatus. Computed tomography apparatuses have a housing to protect the electronic components from contaminants (for example the entrance of fluids) and from external mechanical effects. A patient to be examined or object to be examined is typically positioned in a measurement region, which is located between the essential components of the acquisition system of the computed tomography apparatus (thus between the radiation source and the detector), and is moved through this measurement region. Therefore, the housing is typically located between the radiation source and the detector. In order for the image acquisition to not be negatively affected by the housing, the housing typically has an acquisition window in this region, this acquisition window being arranged annularly around the measurement region and through which the radiation is transmitted. This acquisition window is formed as a ring or a material strip closed to form a ring, and is typically also designated as a radiation passage window or seal ring. The acquisition window is thus part of the casing or housing of the computed tomography apparatus and is situated in the region of the rotating fan beam. Such an acquisition window must have various properties. In particular, the acquisition window must be designed such that the x-ray radiation (and possibly laser light used to identify the acquisition plane, or for positioning) are transmitted without the respective radiations being too significantly weakened. The acquisition window thus should not be too thick, such that—among other things—a higher radiation dose is necessary or the image quality is negatively affected by disruptions or artifacts. Moreover, the acquisition window must be formed of a homogeneous, radiation-resistant material and satisfy the legal ordnances with regard to flame resistance and fire safety. The acquisition window must also be able to compensate for tolerances and misalignments between the front and back casing parts. Furthermore, the acquisition window must be resistant to cleaning and disinfectant agents and have contact protection capability during the operation of the medical apparatus, which means that it must be mechanically stable so that it can withstand a defined load (in particular a load coming from the measurement region). Therefore, such an acquisition window normally has at least one material ring made of a material that is permeable and resistant to x-ray and optical radiation. For example, such a ring can be produced from a material strip of a suitable material that has been joined at the ends thereof by ultrasonic welding, so as to form the ring.

In the case of typical seal rings or acquisition windows that are arranged on a medical apparatus but not permanently attached to the apparatus casing, the problem of the seal ring or acquisition window falling off occurs in the installation or deinstallation of the seal ring. The seal ring or the acquisition window falling off can cause damage to the coating of the seal ring (for example, scratching the surface of the seal ring). Moreover, nearby components can also be damaged. This problem can be solved, for example, by applying adhesive tape between the seal ring and the medical apparatus or the casing parts to which the seal ring is attached, but this solution is time-consuming. Moreover, the adhesive tape must be attached and removed again with care in order to avoid damage to the coating of the seal ring. Moreover, multiple pieces of adhesive tap must be applied so that the seal ring does not fall off. Finally, the adhesive tape can release if it has not been properly applied, so damage to the seal ring or the nearby components due to the seal ring falling off in the installation or in the deinstallation cannot be entirely precluded.

SUMMARY OF THE INVENTION

An object of the present invention is to provide an acquisition window of the aforementioned type for a medical apparatus (in particular for a computed tomography apparatus) that is attached or that can be attached in the installation and/or deinstallation thereof at the medical apparatus such that the acquisition window is stably attached to the medical apparatus but can be detached in a simple manner, so that it is ensured in the installation or in the deinstallation that the acquisition window cannot fall off.

An acquisition window according to the invention has at least one element composed of x-ray-permeable material and an attachment element for releasable attachment of the element to a medical apparatus (in particular a computed tomography apparatus). The at least one attachment element is situated at the side of the element. For example, the element is fashioned as a ring and the attachment element for releasable attachment to the medical apparatus is attached to at least one of the facing sides of the ring. In another example, the element is designed as a band or strip, and the attachment element for releasable attachment to the medical apparatus is attached to at least one side of the band or strip. Thus the acquisition window can be attached to at least one side of the medical apparatus and can be detached from this side again. The acquisition window is advantageously mounted on and/or attached to the or between the casing parts of the medical apparatus (in particular of the computed tomography apparatus). The attachment of the acquisition window to the medical apparatus can be released at any time, such that the acquisition window can be taken out of or removed from the medical apparatus (in particular the computed tomography apparatus) in the event of a service procedure). The installation and disassembly are thus made faster, causing less wear and is simpler, without functional loss or damage to the acquisition window.

Various embodiments of such an attachment element are explained in detail below.

In a first preferred embodiment of the attachment element, the attachment element is formed as a hook. This allows the acquisition window to be attached on at least one side at a point of the medical apparatus (in particular at a point of the casing of the medical apparatus) such that the acquisition window is stably held on the medical apparatus, at least for a defined alignment of the acquisition window. For example, this is the case if the hook is arranged in the upper region of the casing of the medical apparatus and is engaged in this insofar as the acquisition window can rest in the lower region of the casing.

Such a hook advantageously has at least two contiguous parts (a first part and second part) with both parts being formed essentially in the shape of a pin, rod or band and enclosing an angle that is less than 90°. The material of the hook is selected such that the angle enclosed between the first part and second part of the hook can be reversibly changed by exerting pressure on the first part. The material and thus the hook therefore exhibits a certain elasticity that enables it to be hooked and unhooked.

In a preferred version of this embodiment of the attachment element the hook is annular. Such an annular hook has at least two contiguous parts (the first part and second part) wherein both parts are essentially formed in the shape of a band and enclose an angle that is less than 90°. The first part is fashioned as portion of a cone and the second part is fashioned as a cylinder. The material of the hook is also selected such that the angle enclosed between the first part and second part can be reversibly varied by exerting pressure on the first part. The material or the annular hook therefore exhibits a certain elasticity that enables it to be hooked and unhooked. The force with which the acquisition window must be pressed against the surfaces of the casing parts can be modified by the selection of the hook height relative to the casing thickness and/or the selection of the hook shape such that a tight connection is achieved between the casing parts and the acquisition window.

In a second preferred embodiment of the attachment element, the attachment element as a male or female part of a snap fit connection. Such an attachment element is advantageously designed as a male or female snap fit connection element.

A preferred version of such a connection provides an attachment element with a snap fit ball connection. Snap fit ball connections are releasable connections that are produced by engaging mating partners with matching ball geometry (for example an outer ball and an inner ball) in one another, for example. The active principle is a combination of positive and non-positive fit, wherein the engagement of matching, mating partners with matching geometry with one another produces the positive fit and the friction at the contacting surfaces of the respective mating partners produces the non-positive fit. The acquisition window thereby has at least one such attachment element. Such an attachment element is advantageously fashioned as a male or female snap fit ball connection element. This allows the acquisition window to be attached on at least one side at a point of the medical apparatus (in particular at a point of the casing of the medical apparatus) such that the acquisition window can be stably held on the medical apparatus. Moreover, the ball geometry of the mating partners of the connection imparts a degree of mobility. Movement of the acquisition window is thereby enabled that, for example, simplifies positioning of the acquisition window between the casing parts of the medical apparatus (in particular the computed tomography apparatus).

In a further preferred embodiment of such a connection, the attachment element has a snap fit ring connection. A snap fit ring connection is defined (in the manner of a snap fit ball connection) as a releasable connection that is produced by engaging mating partners with matching cylindrical geometry (for example an outer cylinder and an inner cylinder) in one another. As is the case for most snap fit ball connections, the active principle is thereby a combination of positive and non-positive fit. The acquisition window thereby has at least one such attachment element. Such an attachment element is fashioned as a male or female snap fit ring connection element. This allows the acquisition window to be attached on at least one side at a point of the medical apparatus (in particular at a point of the casing of the medical apparatus) such that said acquisition window can be stably held on the medical apparatus. Moreover, due to the positive fit a better handling capability of the acquisition window is achieved in an installation or in a deinstallation, such that the acquisition window does not additionally need to be secured against falling off, which leads to a time savings in the installation or in the deinstallation.

A seal material can additionally be applied between the casing parts and the element and/or the attachment element in order to further improve the seal of the connection. A better handling capability of the acquisition window in an installation or in a deinstallation of the acquisition window is achieved by the attachment element, such that the acquisition window does not additionally need to be secured against falling off, which leads to a time savings in the installation or in the deinstallation.

In a further embodiment of the acquisition window, at least two sides of the element of the acquisition window each have an attachment element. The two sides are preferably two opposite sides of the element, for example the two facing sides of an annular element or the two longest sides of a strip-shaped element made of a suitable material. The acquisition window is attached to the or between the casing parts of the medical apparatus (in particular of the computed tomography apparatus). The attachment of the acquisition window to the medical apparatus thus can be realized from each side, and the acquisition window can be released from each side again at any time, such that the acquisition window can be securely attached to the medical apparatus (in particular the computed tomography apparatus) and taken out and/or removed again, for example in the event of a service procedure. An installation and deinstallation that is even faster, simpler and produces less wear, is thereby enabled without a loss of function or damage to the acquisition window. Moreover, a better attachment of the acquisition window to the medical apparatus (in particular to the computed tomography apparatus) is thereby enabled. In addition, the attachment to an arbitrary side can be released independently of the other side, such that the acquisition window cannot fall off upon opening the medical apparatus from one side. In principle, this also enables a safer opening of the medical apparatus from an arbitrary side.

In another embodiment of the acquisition window, the acquisition window has multiple attachment elements for releasable attachment of the element to a medical apparatus (in particular to a computed tomography apparatus) that are distributed on at least one side of the element. The distribution of the attachment elements on the side is preferably homogeneous or symmetrical. For example, the attachment elements are arranged with a regular spacing. By the use of multiple attachment elements, a distribution of the force effect on the different attachment elements is achieved so that each attachment element is less mechanically stressed. The attachment elements thus can be of smaller dimensions, among other things. Moreover, more materials for the production of the attachment elements are available for use in this embodiment, since the requirements for the mechanical properties of the material to be selected are significantly reduced for each individual attachment element. These attachment elements can all be of the same design in terms of their shape, or some can be different.

In another embodiment of the acquisition window, at least one attachment element is directly attached with the element, thus for example attached with a strip edge or with a facing ring surface of the element. This is preferably not a releasable connection. For example, this (at least one) attachment element is bonded or welded with the element. This connection is advantageously designed to be liquid-tight. All attachment elements of an acquisition window according to the invention are preferably, directly attached to the element. In another embodiment of the acquisition window, the acquisition window additionally has a frame that is mounted on the x-ray-permeable element, advantageously at least on one side of the element. The frame is mounted on the element such that a tight—at least liquid-tight—connection is created between the frame and the element. It is thereby achieved that no fluid (in particular no liquid) can penetrate between the frame and the element. The frame is advantageously bonded or welded with the element. The frame is advantageously fashioned in two parts and is mounted on two different, opposite sides of the x-ray-permeable element. For example, a first part of such a frame is mounted on a first facing side and/or on a second facing side of an annular element. In another example, a first part of such a frame is mounted on a first side and/or on a second, opposite side of a strip-shaped element. Such a frame additionally enables a better handling of the acquisition window.

In another embodiment of the acquisition window the frame has at least one attachment element for releasable attachment to the medical apparatus (in particular to a computed tomography apparatus). The frame preferably has multiple attachment elements that are attached in a homogeneous distribution (for example at regular intervals) on the frame. The at least one attachment element is advantageously attached to the frame—in particular bonded or welded—such that a tight (in particular fluid-tight) connection is created between the at least one attachment element and the frame. This allows the acquisition window to be attached to the medical apparatus on at least one side (advantageously on both sides) so as to be releasable. The acquisition window is attached to, or between, the casing parts of the medical apparatus (in particular of the computed tomography apparatus). The attachment of the acquisition window to the medical apparatus can thereby also be released at any time, such that the acquisition window can be taken out of or removed from the medical apparatus (in particular the computed tomography apparatus) again, for example in the event of service. Installation and deinstallation are thereby made faster, simpler and produce less wear, without loss of function or damage to the acquisition window.

In another embodiment of the acquisition window at least one attachment element for releasable attachment to a medical apparatus (in particular to a computed tomography apparatus) is integrated into the frame.

In a further embodiment of the acquisition window, one side of the element has such a frame while attachment elements are directly connected with the element on the second side. The frame and one side of the x-ray-permeable element have different attachment parts. For example, the acquisition window has on one side a frame with at least one attachment element that is fashioned in the manner of a hook, and on the other hand a (preferably opposite) side of the x-ray-permeable element has at least one attachment element that is fashioned as a male or female part of a snap fit ball connection or snap fit ring connection, or vice versa. For example, an individual or optimized adaptation of the acquisition window to existing systems can be implemented. Moreover, this allows the casing parts between which the acquisition window is arranged and attached to be of differing design. This also allows the acquisition window to better adhere to a specific casing part or to the other part in the installation or in the disassembly, such that—given a proper opening of the casing it is readily apparent to which casing part the acquisition window remains attached. Such a disassembly thus can be planned, and is simple to implement. Moreover, due to the positive fit, a better handling capability of the acquisition window is facilitated in the installation or in the disassembly, such that the acquisition window does not need to be additionally secured against falling off, which leads to a time savings in the installation or in the deinstallation. Moreover, a large degree of freedom in the design of the acquisition window is thereby achieved.

In another embodiments of the acquisition window according to the invention provides that the element has a foil tensioned between two frame parts. The foil, is formed of a suitable material, in particular an x-ray-permeable and x-ray-resistant material. Given the same mechanical resilience, namely orthogonal to the tensioned surface of the foil, a better mechanical resilience of the foil-like element is achieved by tensioning the foil between the frame parts and/or between the casing parts by the respective attachment elements, given the same element thickness or a reduction of the thickness of the element, in particular of the ring or of the strip. A reduction of the thickness of the element enables a reduction of the radiation attenuation, and thus leads to an improvement of the image quality.

Furthermore, the invention concerns a medical apparatus—in particular a computed tomography apparatus—with such an acquisition window according to the invention. The acquisition window is arranged at at least one casing part of the medical apparatus by an attachment element or by multiple attachment elements, and can be attached thereto so as to be releasable again. It is thereby achieved that, in the installation, the acquisition window can be stably attached at a point of the medical apparatus or at one of the casing parts so that the acquisition window can be positioned without thereby being able to fall off. Furthermore, it is achieved that, in the disassembly, the acquisition window remains attached to at least one point of the medical apparatus or one of the casing parts, such that a secure opening of the apparatus is ensured without risk that the acquisition window thereby falls off.

The medical apparatus (in particular the computed tomography apparatus) according to the invention advantageously has at least one casing part that has an inclined edge on the outer contour. The application of a hook-shaped attachment element or of multiple hook-shaped attachment elements is thereby simplified or, respectively, enabled.

The medical apparatus (in particular the computed tomography apparatus) according to the invention has at least one casing part that has at least one male or female snap fit connection element on the outer edge. The frame has a snap fit connection element that extends over the entire edge of the casing geometry, and the connection geometry corresponds to a respective frame geometry. The connection geometry of the casing parts is thus the negative of the frame geometry.

The casing can have a recess for the acquisition window (in particular for the frame of the acquisition window) that is realized such that at least a portion of the frame can be accommodated with positive fit in the recess, at least in one direction. The casing can have a recess for the acquisition window that is realized such that at least a portion of the edge of the element can be accommodated with positive fit in the recess, at least in one direction. A tight connection is thereby enabled between the respective frame or element edges and the casing surfaces over the entire circumference. The recess is realized such that, after mounting the acquisition window in the recess, at least one gap between the respective frame or the element edges and the casing surfaces is present over the entire circumference, which gap can be used to accommodate an adhesive or sealant. A tight connection between the respective frame surfaces and casing surfaces is thereby achieved over the entire circumference.

The medical apparatus according to the invention with an acquisition window according to the invention is advantageously a computed tomography apparatus.

BRIEF DESCRIPTION OF THE DRAWINGS

FIG. 2 is a schematic section through the gantry of a computed tomography apparatus in the region of an installed acquisition window according to the invention.

FIG. 3 is a schematic section through the gantry of a computed tomography apparatus in the region of an installed acquisition window according to the invention.

DESCRIPTION OF THE PREFERRED EMBODIMENTS

Figure 1:
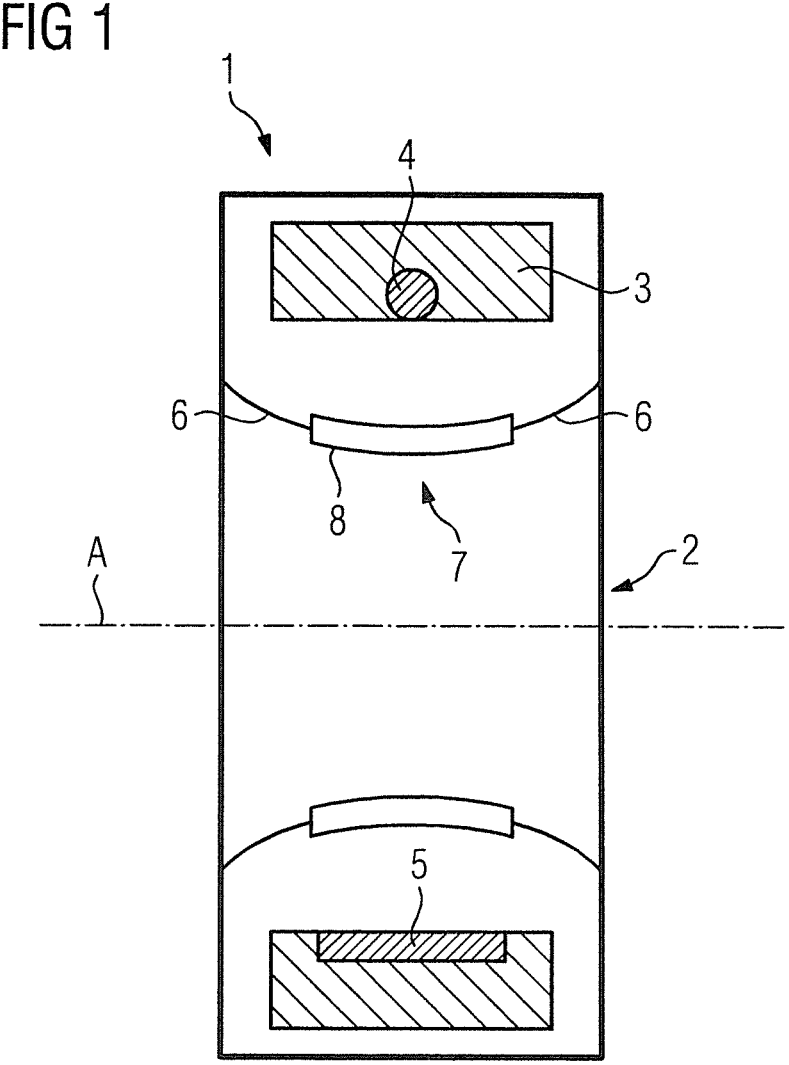
FIG. 1 is a schematic section through the gantry of a computed tomography apparatus.

FIG. 1 is a schematic section of a computed tomography apparatus (not further shown) in the region of the gantry 1. The computed tomography apparatus has a circular opening 2 that is arranged around the measurement region. A subject to be examined or a patient to be examined can be moved into this region. The gantry 1 has a rotating part 3. Part of the rotating part 3 is, among other things, an acquisition system that has at least one radiation source 4 and a detector 5, which form said acquisition system of the computed tomography apparatus. The rotating part 3 is borne such that it can rotate around the axis (A) of symmetry of the central opening 2 of the apparatus. The housing of the computed tomography apparatus has an annular acquisition window 7 that is arranged around the measurement region and through which the radiation emitted by the source 4 passes. The housing of the computed tomography apparatus, moreover, has casing parts 6 between which the acquisition window 7 is arranged. The acquisition window 7 serves (among other things) as a protection of the highly sensitive, rotating acquisition system 3, 4, 5 against mechanical effects and contaminants, and exhibits homogeneous material properties.

FIG. 2 shows a section through the gantry 1 of a computed tomography apparatus in the region of the acquisition window 7 according to the invention, wherein the acquisition window 7 is attached between the casing parts 6 by means of attachment elements 9 at these casing parts 6. In this shown example, the acquisition window 7 has a two-part frame 10 and an annular, x-ray-permeable element 8. The annular, x-ray-permeable element 8 and the two-part frame 10 are thereby bonded with one another. In this exemplary embodiment, the attachment elements 9 are fashioned as hooks. The hooks thereby have two contiguous parts 9a and 9b. The acquisition window 7 thereby has a variable number of such hooks on the complete circumference of the frame geometry. For example, these are made from plastic or metal. The edges of the casing parts 6 thereby have an inclined edge which facilitates the hooking or the engagement of the hooks. The casing parts 6 moreover have a receptacle for accommodating the frame of the acquisition window 7. In this exemplary embodiment, a sealant material 12 which enables a tight connection between the casing parts 6 and the frame 10 is applied in a gap 11 between the casing parts 6 and the frame parts 10, at least in part. The seal advantageously has a square profile. For example, the acquisition window 7 is compressed and placed in-between the casing parts 6 before the installation so that, by pressing on the casing and subsequent deployment of the hooks, these engage at the edge of the casing and ensure a firm seating of the acquisition window 7. Such an acquisition window 7 can therefore be installed between the casing parts 6 without needing to remove other casing parts from the apparatus or needing to open the apparatus.

FIG. 3 shows a section through the gantry 1 of a computed tomography apparatus in the region of the acquisition window 7 according to the invention, wherein the acquisition window 7 between the casing parts 6 is attached to these by the attachment elements 9. The acquisition window 7 has a two-part frame 10 and an annular, x-ray-permeable element 8. The annular, x-ray-permeable element 8 and the frame 10 are bonded with one another. In this exemplary embodiment, the attachment elements 9 are fashioned as a female part of a snap fit ball connection or snap fit ring connection and are integrated into the frame 10. The connection geometry of the casing corresponds to the negative of the frame geometry; in this presented example, the connection geometry of the casing 6 is thereby fashioned as a male part of a snap fit ball connection or snap fit ring connection. In an embodiment (not shown), the frame geometry is fashioned as a male part of a snap fit ball connection or snap fit ring connection while the connection geometry of the casing is fashioned as a female part of a snap fit ball connection or snap fit ring connection. A positive fit and negative fit of the frame geometry with the connection geometry of the casing parts arise via the snap fit connection, which positive and negative fit ensure that the acquisition window 7 does not detach from the casing 6 in an installation or, respectively, in a disassembly. The positive fit moreover ensures a tight connection between frame 10 and connection geometry of the casing parts 6. Furthermore, the frame geometry comprises at least one partially elastic material which takes on an additional function of the sealing of the connection.

Although modifications and changes may be suggested by those skilled in the art, it is the intention of the inventors to embody within the patent warranted hereon all changes and modifications as reasonably and properly come within the scope of their contribution to the art.

We claim as our invention:

1. An acquisition window for a medical apparatus comprising an x-ray source and an apparatus housing in which the x-ray source is situated, said acquisition window comprising:
    a window element comprised of x-ray-permeable material, said window element comprising a plurality of window sides; and
    at least one attachment element that releasably attaches at least one of said sides of said window element to said housing of said medical apparatus.

2. An acquisition window as claimed in claim 1 wherein said at least one attachment element is configured as a hook.

3. An acquisition window as claimed in claim 1 wherein at least one attachment element comprises a male part and a mating female part forming a snack fit connection of said at least one side of said window element to said apparatus housing.

4. An acquisition window as claimed in claim 3 wherein said snap fit connection is selected from the group consisting of snap fit ring connections and snap fit ball connections.

5. An acquisition window as claimed in claim 1 comprising at least two attachment elements respectively attaching at least two of said window sides to said apparatus housing.

6. An acquisition window as claimed in claim 1 comprising a plurality of said releasable attachment elements, said plurality of releasable attachment elements being spatially distributed along said at least one window side in a distribution that equally distributes, among individual attachment elements in said plurality of attachment elements, a total force applied by said plurality of attachment elements to attach said at least one window side to said apparatus housing.

7. An acquisition window as claimed in claim 1 wherein said at least one attachment element is directly attached to said x-ray permeable material of said window element.

8. An acquisition window as claimed in claim 1 comprising frame that surrounds said window element and that is attached to the x-ray permeable material of said window element.

9. An acquisition window as claimed in claim 8 wherein said at least one attachment element attaches said frame at said at least one window side to said apparatus housing.

10. An acquisition window as claimed in claim 9 wherein said attachment element is mechanically integrated into said frame.

11. An acquisition window as claimed in claim 1 wherein said at least one attachment element is formed as a strip.

12. An acquisition window as claimed in claim 1 wherein said at least one attachment element is formed as a ring.

13. An acquisition window as claimed in claim 1 comprising at least two attachment elements respectively disposed at least two opposite window sides, and wherein said x-ray permeable material is a foil that is tensioned between said at least two attachment elements.

14. A medical apparatus comprising:
an x-ray source situated in an apparatus housing, said x-ray source emitting an x-ray beam; and
an acquisition window comprising a window element comprised of an x-ray-permeable material disposed in a path of said x-ray beam, said window element comprising a plurality of sides, and at least one attachment element that releasably attaches at least one window side of said window element to said apparatus housing.

15. A medical apparatus as claimed in claim 14 comprising a plurality of apparatus components that, in combination with said x-ray source, are configured to acquire computed tomography data from a subject situated in said path of said x-ray beam.

\* \* \* \* \*